United States Patent
Lee et al.

(10) Patent No.: US 12,350,682 B2
(45) Date of Patent: Jul. 8, 2025

(54) MICROELECTRODE DEVICE, MICROFLUIDIC CHIP, AND MICROFLUIDIC EXAMINATION METHOD

(71) Applicant: NATIONAL YANG MING CHIAO TUNG UNIVERSITY, Hsinchu (TW)

(72) Inventors: Chen-Yi Lee, Hsinchu (TW); Yun-Sheng Chan, Hualien (TW)

(73) Assignee: National Yang Ming Chiao Tung University, Hsinchu (TW)

( * ) Notice: Subject to any disclaimer, the term of this patent is extended or adjusted under 35 U.S.C. 154(b) by 727 days.

(21) Appl. No.: 17/540,868

(22) Filed: Dec. 2, 2021

(65) Prior Publication Data
US 2022/0297131 A1     Sep. 22, 2022

Related U.S. Application Data

(60) Provisional application No. 63/163,226, filed on Mar. 19, 2021.

(30) Foreign Application Priority Data

May 28, 2021   (TW) .................................. 110119564

(51) Int. Cl.
*B01L 7/00*     (2006.01)
*B01L 3/00*     (2006.01)
(Continued)

(52) U.S. Cl.
CPC .............. *B01L 7/525* (2013.01); *B01L 3/5027* (2013.01); *C12Q 3/00* (2013.01);
(Continued)

(58) Field of Classification Search
CPC .. B01L 3/5027; B01L 7/525; B01L 3/502761; B01L 2300/0645;
(Continued)

(56) References Cited

U.S. PATENT DOCUMENTS 11,016,053 B2 *   5/2021  Huff ................... B01L 3/502761
2011/0247938 A1 * 10/2011  Wang ................ B01L 3/502792
                                                                    204/603
(Continued)

FOREIGN PATENT DOCUMENTS

CN          103194383 A     7/2013
WO      WO 2019/226919 A1   11/2019

*Primary Examiner* — Shogo Sasaki
(74) *Attorney, Agent, or Firm* — Christensen, Fonder, Dardi & Herbert PLLC; John P. Fonder

(57) ABSTRACT

A microelectrode device, microfluidic chip, and microfluidic examination method are provided. The microfluidic chip includes a top plate and a microelectrode dot array having several microelectrode devices. Each microelectrode device includes a microfluidic electrode, heating electrode, and control circuit. The control circuit includes a microfluidic control and location sensing circuit, storage circuit, and temperature control circuit. The microfluidic control and location sensing circuit moves a sample within an enabling period of a microfluidic control signal and detects a capacitance value between the microfluidic electrode and the top plate within an enabling period of a location control signal. The storage circuit outputs the capacitance value, reads in the sample operation setup, and reads in the heating control setup within different enabling periods of the clock. The temperature control circuit determines either on or off according to the heating control setup within an enabling period of a heating control signal.

19 Claims, 11 Drawing Sheets

(51) Int. Cl.
*C12Q 3/00* (2006.01)
*G01N 35/00* (2006.01)

(52) U.S. Cl.
CPC .. *G01N 35/00584* (2013.01); *B01L 2200/025* (2013.01); *B01L 2200/143* (2013.01); *B01L 2300/0645* (2013.01); *B01L 2300/0819* (2013.01); *B01L 2300/1805* (2013.01); *G01N 2035/00376* (2013.01)

(58) Field of Classification Search
CPC ..... B01L 2300/0819; B01L 2300/1805; B01L 2200/025; B01L 2200/143; G01N 35/00584; G01N 2035/00376; C12Q 3/00
See application file for complete search history.

(56) References Cited

U.S. PATENT DOCUMENTS

2018/0258379 A1* 9/2018 Zahn ................. G01N 15/1023
2022/0395836 A1* 12/2022 Sall ....................... B01L 3/5453

* cited by examiner

MICROELECTRODE DEVICE, MICROFLUIDIC CHIP, AND MICROFLUIDIC EXAMINATION METHOD

PRIORITY CLAIM

This application claims priorities to U.S. Provisional Patent Application No. 63/163,226 filed on Mar. 19, 2021 and Taiwan Patent Application No. 110119564 filed on May 28, 2021, which are hereby incorporated by reference in its entirety.

FIELD OF THE INVENTION

The present invention relates to microelectrode devices, microfluidic chips, and microfluidic examination methods. More specifically, the present invention relates to programmable microelectrode devices, microfluidic chips, and microfluidic examination methods in terms of temperature control.

BACKGROUND OF THE INVENTION

Biomedical analyses and tests (e.g., protein analyses, disease diagnoses) by microfluidic chips usually require heating a to-be-tested sample to one or more particular temperatures during the examination procedure. Taking the Polymerase Chain Reaction (PCR) test as an example, the three main steps (i.e., Deoxyribonucleic Acid (DNA) denaturation, annealing, and extension) have to be executed repeatedly in order to generate tremendous copies of a particular section of DNA. As the previously mentioned three main steps require different temperatures, thermal cycling is necessary in the test procedure. Conventionally, thermal cycling can be achieved by optical manners (e.g., laser) or heating board(s), however, all require an additional feedback mechanism to control temperature effectively. Moreover, the heating area(s) configured by the previously mentioned heating mechanism is/are fixed. Therefore, it is not adaptive to different applications, and the design of microchannels are bounded.

Another difficulty of using microfluidic chips in various biomedical analyses and tests is that the market is quite limited. This is because conventional microfluidic chips are customized for specific fields or for screening specific diseases. Hence, mass production is not feasible and practical.

Based on the aforementioned reasons, a microfluidic examination technique that can control examination temperature flexibly for different examination procedures and that can be applied to various fields and various examination procedures is in urgent need.

SUMMARY OF THE INVENTION

An objective of the present invention is to provide a microelectrode device, which comprises a microfluidic electrode, a heating electrode, and a control circuit. The microfluidic electrode is arranged under a top plate, the heating electrode is arranged under the microfluidic electrode, and the control circuit is arranged under the heating electrode. The control circuit comprises a temperature control circuit, a storage circuit, and a microfluidic control and location sensing circuit. The temperature control circuit is coupled to the heating electrode, and the microfluidic control and location sensing circuit is coupled to the microfluidic electrode. The storage circuit reads in a sample operation configuration during a first enabling time interval of a clock. The microfluidic control and location sensing circuit performs a sample operation according to the sample operation configuration during a second enabling time interval of a microfluidic control signal. The microfluidic control and location sensing circuit detects a capacitance value between the top plate and the microfluidic electrode and then stores the capacitance value in the storage circuit during a third enabling time interval of a location control signal. The storage circuit outputs the capacitance value during a fourth enabling time interval of the clock and reads in a heating control configuration during a fifth enabling time interval of the clock. The temperature control circuit determines a status of a switch of the temperature control circuit according to the heating control configuration during a sixth enabling time interval of a heating control signal.

Another objective of the present invention is to provide a microfluidic chip, which comprises a top plate and a microelectrode dot array. The microelectrode dot array is arranged under the top plate and comprises a plurality of microelectrode devices connected in a series. Each of the microelectrode devices comprises a microfluidic electrode, a heating electrode, and a control circuit. Each of the microfluidic electrodes is arranged under the top plate, each of the heating electrodes is arranged under the corresponding microfluidic electrode, and each control circuit is arranged under the corresponding heating electrode. Each of the control circuits comprises a temperature control circuit, a storage circuit, and a microfluidic control and location sensing circuit. Each of the temperature control circuits is coupled to the corresponding heating electrode, and each of the microfluidic control and location sensing circuits is coupled to the corresponding microfluidic electrode. Each of the storage circuits reads in a corresponding sample operation configuration during a first enabling time interval of a clock. Each of the microfluidic control and location sensing circuits performs a corresponding sample operation according to the corresponding sample operation configuration during a second enabling time interval of a microfluidic control signal. Each of the microfluidic control and location sensing circuits detects a corresponding capacitance value between the top plate and the corresponding microfluidic electrode and then stores the corresponding capacitance value in the corresponding storage circuit during a third enabling time interval of a location control signal. Each of the storage circuits outputs the corresponding capacitance value during a fourth enabling time interval of the clock and reads in a corresponding heating control configuration during a fifth enabling time interval of the clock. Each of the temperature control circuits determines a status of a switch of the temperature control circuit according to the corresponding heating control configuration during a sixth enabling time interval of a heating control signal.

A further objective of the present invention is to provide a microfluidic examination method, which is for use in a microfluidic chip. The microfluidic chip comprises a top plate and a microelectrode dot array, wherein the microelectrode dot array is arranged under the top plate. The microelectrode dot array comprises a plurality of microelectrode devices connected in a series, and each of the microelectrode devices comprises a microfluidic electrode, a heating electrode, and a control circuit. Each of the microfluidic electrodes is arranged under the top plate, each of the heating electrodes is arranged under the corresponding microfluidic electrode, and each of the control circuits is arranged under the corresponding heating electrode. Each of the control circuits comprises a microfluidic control and location sensing circuit, a storage circuit, and a temperature control circuit. Each of the microfluidic control and location sensing circuits is coupled to the corresponding microfluidic electrode, and each of the temperature control circuits is coupled to the corresponding heating electrode. The microfluidic examination method comprises the following step (a), step (b), step (c), step (d), and step (e).

Step (a) provides a clock to the storage circuits. Step (b) provides a microfluidic control signal to the microfluidic control and location sensing circuits. Step (c) provides a location control signal to the microfluidic control and location sensing circuits. Step (d) provides a plurality of sample operation configurations, wherein the sample operation configurations correspond to the microelectrode devices one-to-one. Step (e) provides a plurality of heating control configurations, wherein the heating control configurations correspond to the microelectrode devices one-to-one. Each of the storage circuits reads in the corresponding sample operation configuration during a first enabling time interval of a clock. Each of the microfluidic control and location sensing circuits performs a corresponding sample operation according to the corresponding sample operation configuration during a second enabling time interval of the microfluidic control signal. Each of the microfluidic control and location sensing circuits detects a corresponding capacitance value between the top plate and the corresponding microfluidic electrode and then stores the corresponding capacitance value in the corresponding storage circuit during a third enabling time interval of the location control signal. Each of the storage circuits outputs the corresponding capacitance value during a fourth enabling time interval of the clock. Each of the storage circuits reads in a corresponding heating control configuration during a fifth enabling time interval of the clock. Each of the temperature control circuits determines a status of a switch of the corresponding temperature control circuit according to the corresponding heating control configuration during a sixth enabling time interval of a heating control signal.

According to the microelectrode device provided by the present invention, the control circuit therein comprises a microfluidic control and location sensing circuit, a temperature control circuit, and a storage circuit, and the microfluidic control and location sensing circuit, the temperature control circuit, and the storage circuit may receive different signals. Therefore, each of the signals may be designated a corresponding enabling time interval to perform operations related to the microfluidic examination, including reading in a sample operation configuration, performing a sample operation, detecting a to-be-tested sample, outputting the detection result regarding the to-be-tested sample, reading in the heating control configuration, and giving off heat to the to-be-tested sample. The microfluidic chip provided by the present invention comprises a microelectrode dot array having a plurality of microelectrode devices connected in a series. Since the microfluidic control and location sensing circuit, the temperature control circuit, and the storage circuit comprised in each of the microelectrode devices may receive different signals, each of the signals may be designated a corresponding enabling time interval, and different sample operation configurations and different heating control configurations may be provided to different microelectrode devices. Therefore, operations related to more complicated microfluidic examinations can be achieved. As a result, the microelectrode devices, microfluidic chips, and microfluidic examination methods provided by the present invention can be applied to various fields and various examination procedures. When performing microfluidic examinations by the microelectrode devices, microfluidic chips, and microfluidic examination methods provided by the present invention, examination temperature can be adjusted flexibly for different examination procedures.

The detailed technology and preferred embodiments implemented for the subject invention are described in the following paragraphs accompanying the appended drawings for a person having ordinary skill in the art to well appreciate the features of the claimed invention.

BRIEF DESCRIPTION OF THE DRAWINGS

FIG. 2E is a schematic view of the sample operation configurations for moving and mixing the to-be-tested sample(s);

DETAILED DESCRIPTION

In the following descriptions, the microelectrode devices, microfluidic chips, and microfluidic examination methods of the present invention will be explained with reference to certain embodiments thereof. However, these embodiments are not intended to limit the present invention to any specific environment, application, or implementations described in these embodiments. Therefore, descriptions of these embodiments are for the purpose of illustration rather than to limit the scope of the present invention. It should be noted that, in the following embodiments and the attached drawings, elements unrelated to the present invention are omitted from depiction. In addition, dimensions of and dimensional scales between individual elements in the attached drawings are provided only for ease of depiction and illustration but not to limit the scope of the present invention.

Figure 1A:
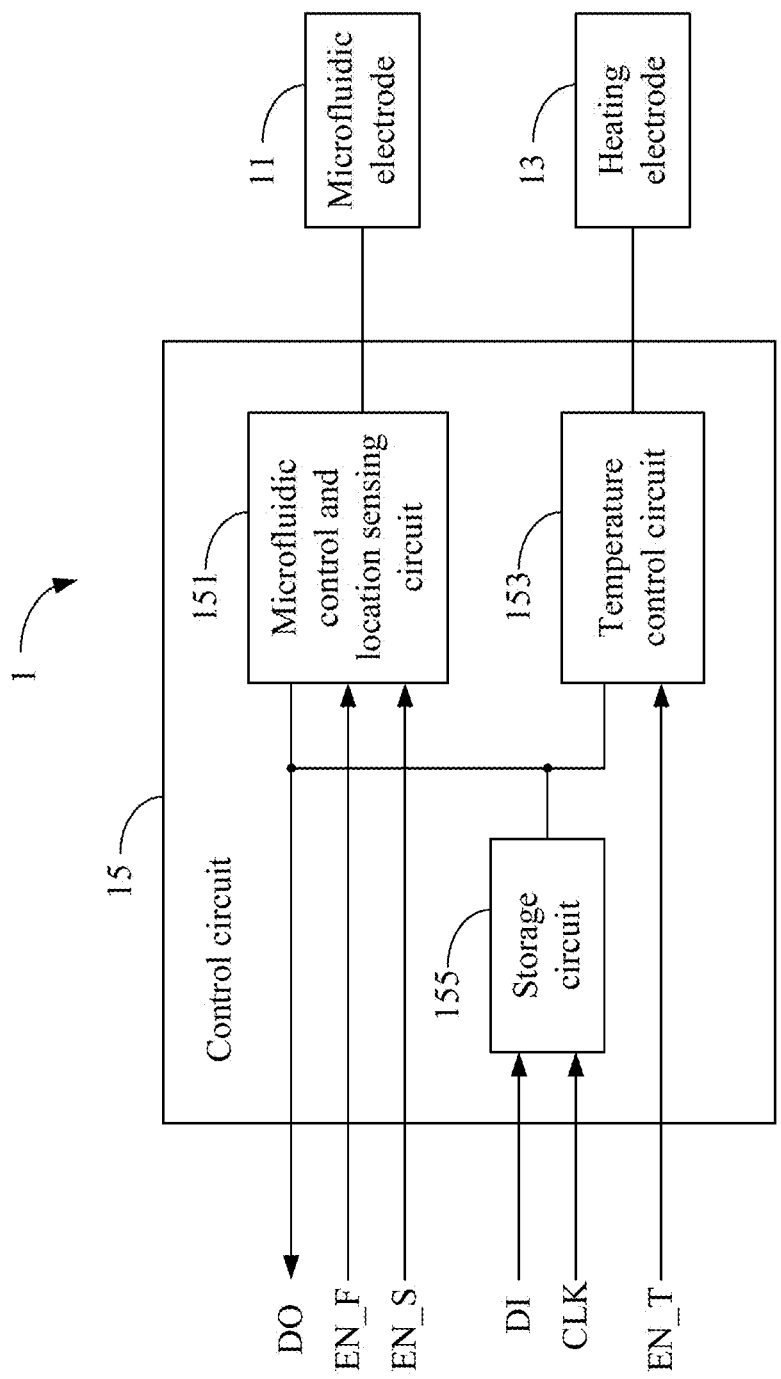
FIG. 1A illustrates the circuit block diagram of the microelectrode device 1 in the first embodiment of the present invention.
Figure 1B:
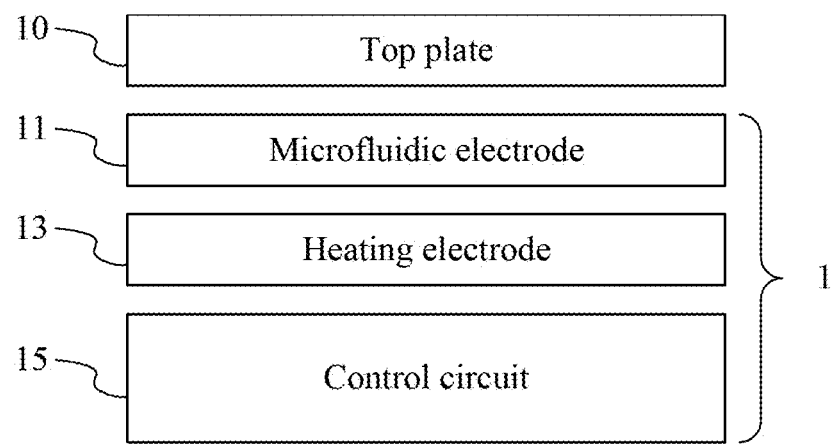
FIG. 1B illustrates the side sectional view of the microelectrode device 1 in the first embodiment of the present invention.

The first embodiment of the present invention is a microelectrode device 1, and the circuit block diagram and the side sectional view of the microelectrode device 1 are illustrated in FIG. 1A and FIG. 1B respectively. The microelectrode device 1 comprises a microfluidic electrode 11, a heating electrode 13, and a control circuit 15, wherein the microfluidic electrode 11 is arranged under a top plate 10, the heating electrode 13 is arranged under the microfluidic electrode 11, and the control circuit 15 is arranged under the heating electrode 13. The top plate 10 may be formed by a conductive material, e.g., an Indium Tin Oxide (ITO) glass. Please note that the size of the microelectrode device 1 is not limited in the present invention. Nevertheless, in some embodiments, the area of the top surface of the microelectrode device 1 may be 2,500 $\mu m^2$.

Figure 1C:
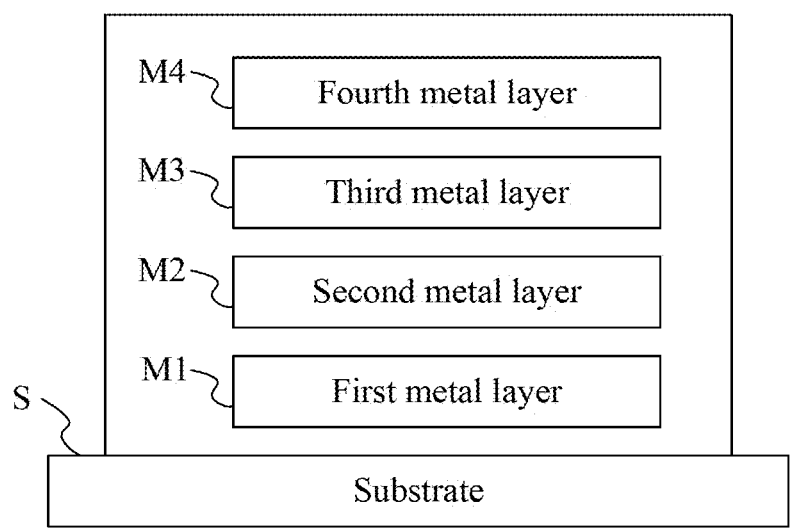
FIG. 1C illustrates a schematic view of a semiconductor structure having four metal layers.
Figure 1D:
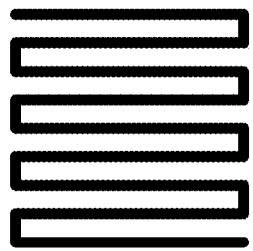
FIG. 1D illustrates a schematic view of the shape of the heating electrode in some embodiments of the present invention.

In some embodiments, a semiconductor process that can form the semiconductor structure shown in FIG. 1C may be adopted to implement the microelectrode device 1. The semiconductor structure shown in FIG. 1C comprises a substrate S, and on top of the substrate S are four metal layers, including the first metal layer M1, the second metal layer M2, the third metal layer M3, and the fourth metal layer M4 from the bottom to the top. In those embodiments, the control circuit may be formed at the first metal layer M1 and the second metal layer M2, the heating electrode 13 may be formed at the third metal layer M3, and the microfluidic electrode 11 may be formed at the fourth metal layer M4. In some embodiments, the shape of the heating electrode 13 may look like the one shown in FIG. 1D.

In this embodiment, the control circuit 15 comprises a microfluidic control and location sensing circuit 151, a temperature control circuit 153, and a storage circuit 155. The microfluidic control and location sensing circuit 151 is coupled to the microfluidic electrode 11, and the temperature control circuit 153 is coupled to the heating electrode 13. In addition, the microfluidic control and location sensing circuit 151, the temperature control circuit 153, and the storage circuit 155 are coupled to each other. The microfluidic control and location sensing circuit 151 is configured to receive a microfluidic control signal EN_F and a location control signal EN_S. The storage circuit 155 is configured to receive a clock CLK, receive and store an input signal DI, and provide an output signal DO. The temperature control circuit 153 is configured to receive a heating control signal EN_T. Furthermore, a voltage signal VS may be provided at the top of the top plate 10.

Figure 1E:
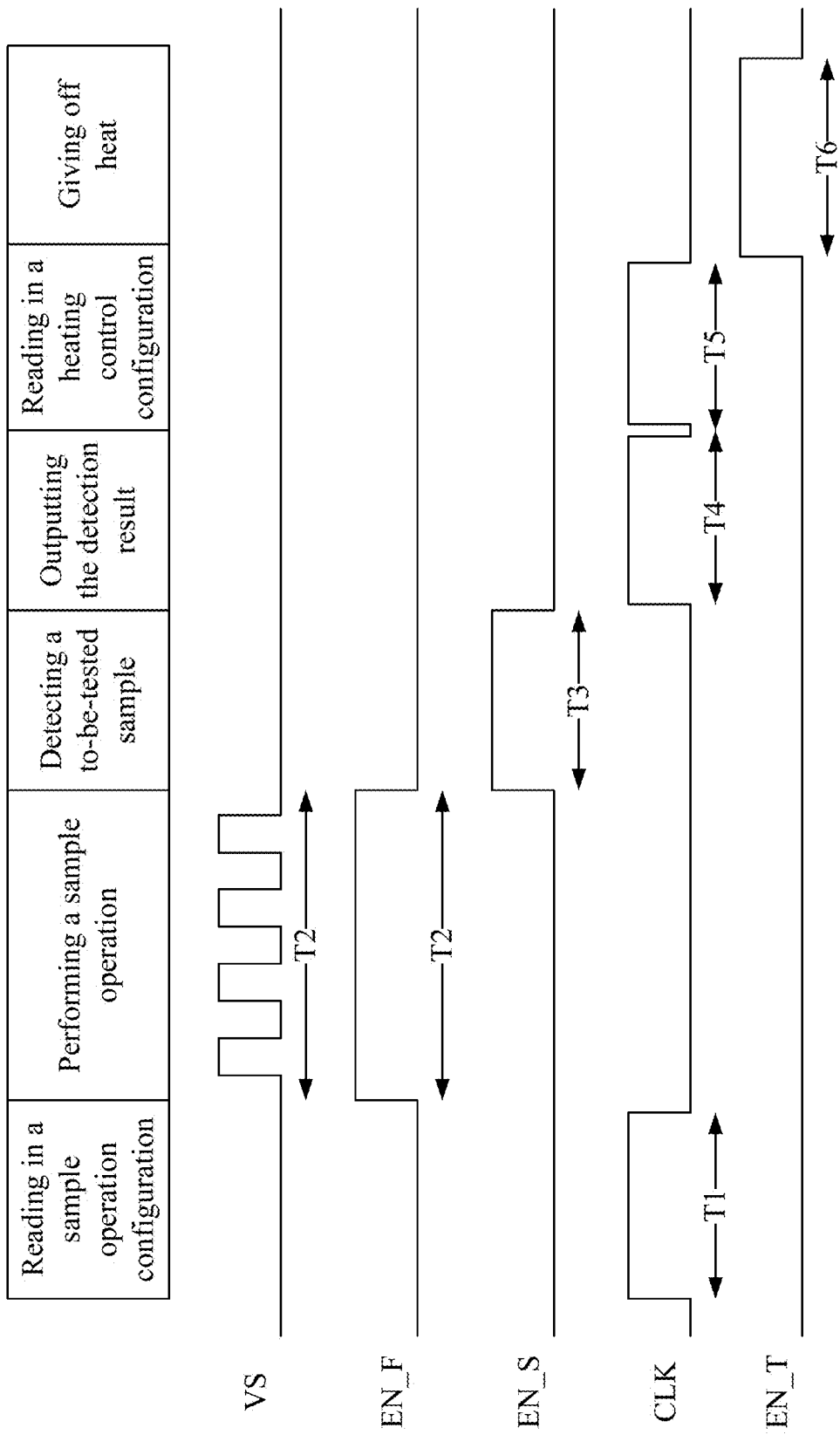
FIG. 1E illustrates the timing diagram of the signals that may be adopted to control the actions of the microelectrode device 1 within an examination cycle in some embodiments.

In some embodiments, the timing diagram of the signals shown in FIG. 1E may be adopted to control the actions of the microelectrode device 1 within an examination cycle. To be more specific, an examination cycle may comprise the enabling time intervals T1, T2, T3, T4, T5, T6, wherein the enabling time interval T2 is later than the enabling time interval T1, the enabling time interval T3 is later than the enabling time interval T2, the enabling time interval T4 is later than the enabling time interval T3, the enabling time interval T5 is later than the enabling time interval T4, and the enabling time interval T6 is later than the enabling time interval T5. As shown in FIG. 1E, the clock CLK corresponds to the enabling time intervals T1, T4, T5, the voltage signal VS and the microfluidic control signal EN_F both correspond to the enabling time interval T2, the location control signal EN_S corresponds to the enabling time interval T3, and the heating control signal EN_T correspond to the enabling time interval T6. Please note that the voltage level of a signal (e.g., the clock CLK, the voltage signal VS, the microfluidic control signal EN_F, the location control signal EN_S, and the heating control signal EN_T) may be high in the corresponding enabling time interval, and the voltage level of a signal in the corresponding non-enabling time interval must be low.

The actions performed by the microelectrode device 1 under the control of this timing diagram of signals will be detailed in the following paragraphs. During the enabling time interval T1 of the clock CLK, the storage circuit 155 reads in a sample operation configuration (not shown) from the input signal DI. The sample operation configuration is used for indicating the sample operation to be performed by the microfluidic control and location sensing circuit 151 during the enabling time interval T2. For example, the numerical values "0" and "1" may be used as the content of the sample operation configuration, wherein the numerical value "1" is used to instruct the microfluidic control and location sensing circuit 151 to act, and the numerical value "0" is used to instruct the microfluidic control and location sensing circuit 151 not to act. Afterwards, during the enabling time interval T2, the microfluidic control and location sensing circuit 151 performs a sample operation (i.e., a microfluidic operation) according to the sample operation configuration. For example, the sample operation may be moving a to-be-tested sample, cutting a to-be-tested sample, and mixing to-be-tested samples.

During the enabling time interval T3 of the location control signal EN_S, the microfluidic control and location sensing circuit 151 determines whether there is a to-be-tested sample. To be more specific, during the enabling time interval T3 of the location control signal EN_S, the microfluidic control and location sensing circuit 151 detects a capacitance value (not shown) between the top plate 10 and the microfluidic electrode 11 and stores the capacitance value in the storage circuit 155. The capacitance value reflects whether there is a to-be-tested sample between the top plate 10 and the microfluidic electrode 11. If using the numerical values "0" and "1" as the detected capacitance value, the numerical value "1" indicates that there is a to-be-tested sample between the top plate 10 and the microfluidic electrode 11 and the numerical value "0" indicates that there is no to-be-tested sample between the top plate 10 and the microfluidic electrode 11. Next, during the enabling time interval T4 of the clock CLK, the storage circuit 155 outputs the capacitance value (i.e., outputs the result of determining whether there is a to-be-tested sample).

Following that, during the enabling time interval T5 of the clock CLK, the storage circuit 155 reads in a heating control configuration (not shown) from the input signal DI. The heating control configuration is used for configuring a status of a switch of the temperature control circuit 153, e.g., the numerical values "1" and "0" may be used for configuring the status to be "on" and "off" respectively. During the enabling time interval T6 of the heating control signal EN_T, the temperature control circuit 153 configures the status of the switch of the temperature control circuit 153 according to the heating control configuration. If the heating control configuration indicates that the status of the switch of the temperature control circuit 153 should be on (e.g., the numerical value of the heating control configuration is "1"), the temperature control circuit 153 configures its switch to be on so that the heating electrode 13 can give off heat. If the heating control configuration indicates that the status of the switch of the temperature control circuit 153 should be off (e.g., the numerical value of the heating control configuration is "0"), the temperature control circuit 153 configures its switch to be off so that the heating electrode 13 does not function (i.e., give off no heat). According to the previously mentioned mechanisms, the microelectrode device 1 can reach a particular temperature to perform a particular microfluidic examination.

According to the above descriptions, the control circuit 15 of the microelectrode device 1 comprises the microfluidic control and location sensing circuit 151, the temperature control circuit 153, and the storage circuit 155, and the microfluidic control and location sensing circuit 151, the temperature control circuit 153, and the storage circuit 155 may receive different signals. Each of the signals may be designated a corresponding enabling time interval to perform operations related to the microfluidic examination, including reading in the sample operation configuration, performing a sample operation, detecting a to-be-tested sample, outputting the detection result regarding the to-be-tested sample, reading in the heating control configuration, and giving off heat to the to-be-tested sample. Therefore, when performing microfluidic examinations by the microelectrode device 1, examination temperature can be adjusted flexibly for different examination procedures. As a consequence, the microelectrode device 1 can be applied to various fields and various examination procedures.

Figure 2A:
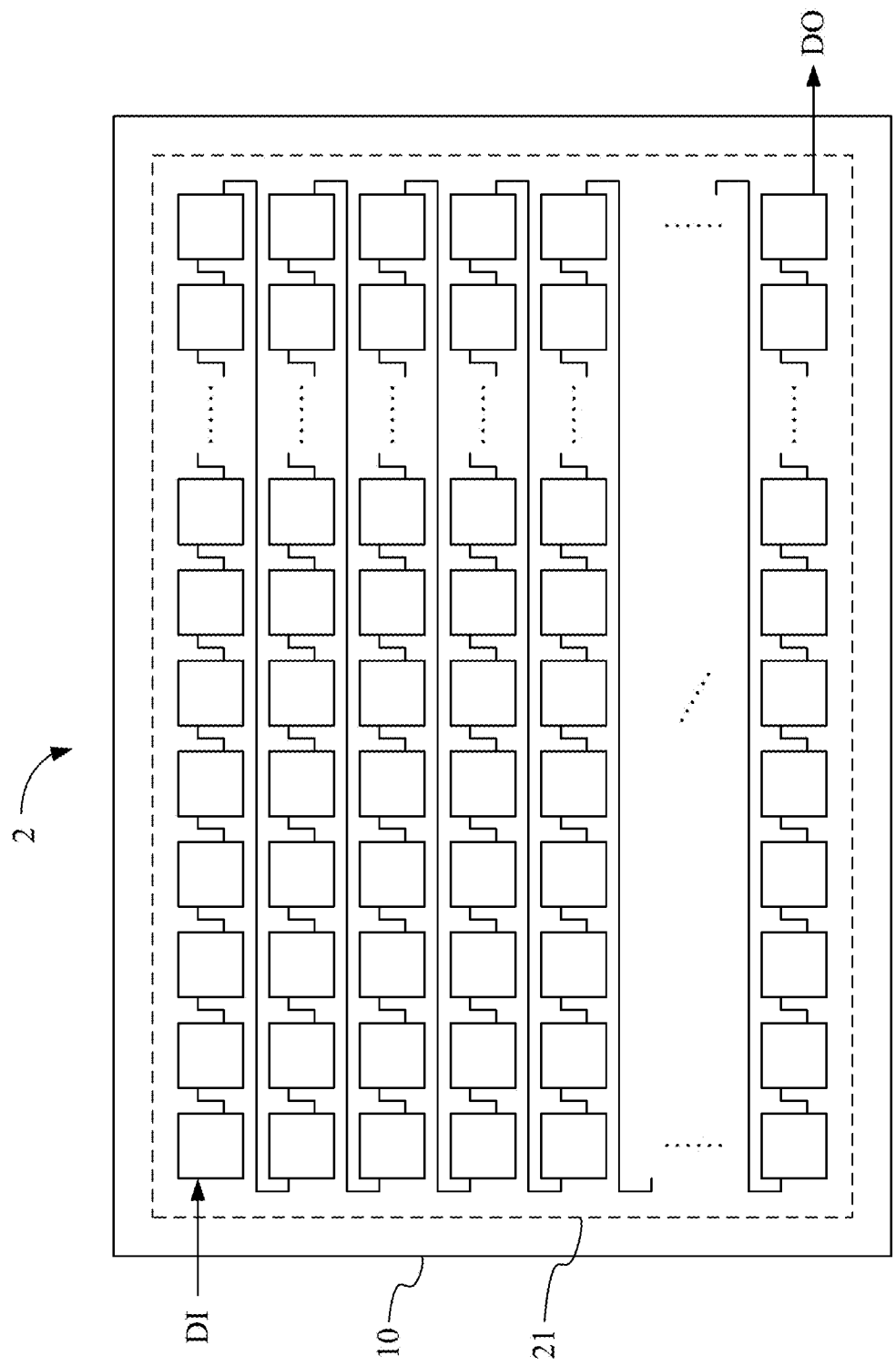
FIG. 2A illustrates the top view of the microfluidic chip 2 in the second embodiment of the present invention.
Figure 2B:
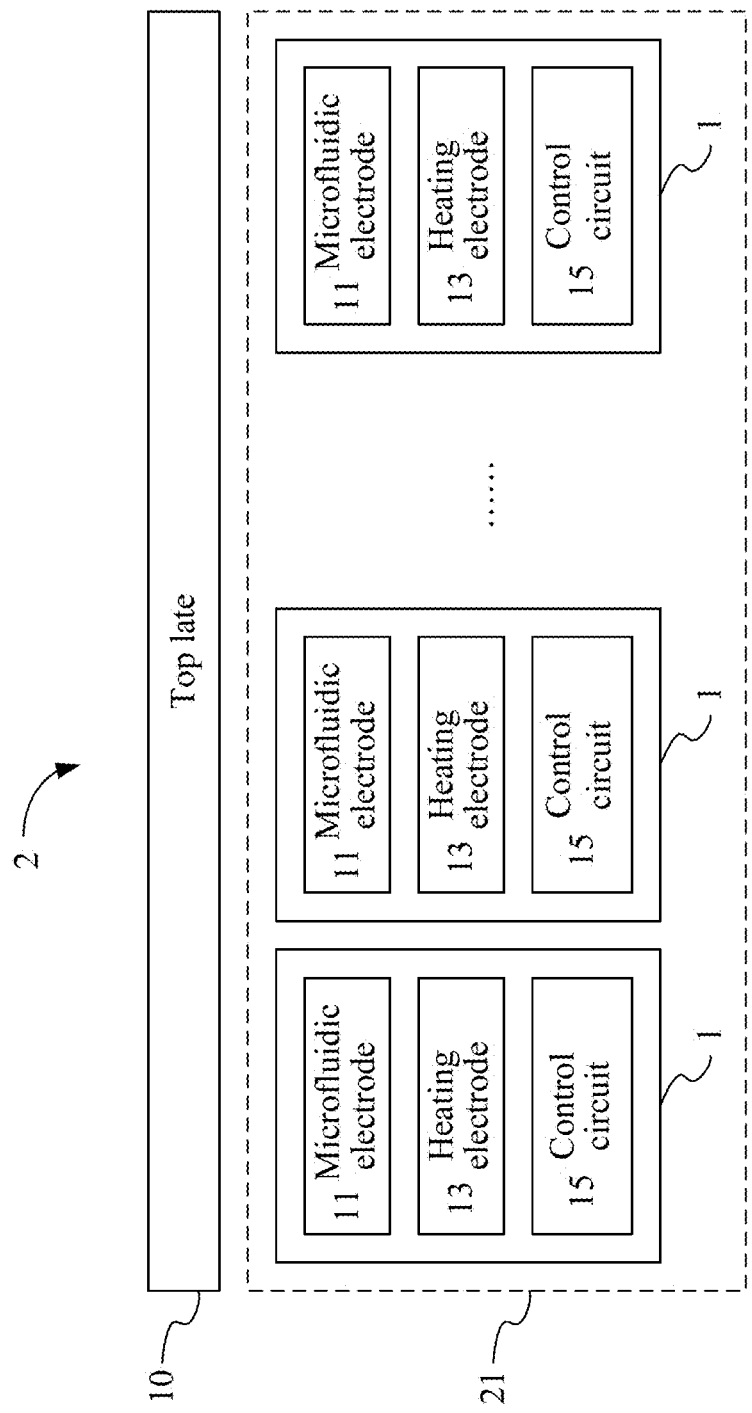
FIG. 2B illustrates the side sectional view of the microfluidic chip 2 in the second embodiment of the present invention.

The second embodiment of the present invention is a microfluidic chip 2. The top view and the side sectional view of the microfluidic chip 2 are illustrated in FIG. 2A and FIG. 2B respectively. The microfluidic chip 2 comprises a top plate 10 and a microelectrode dot array 21, wherein the microelectrode dot array 21 is arranged under the top plate 10 and comprises a plurality of microelectrode devices 1 connected in a series. In FIG. 2A, each square represents a microelectrode device 1, wherein each of the microelectrode devices 1 has an input terminal and an output terminal. For each of the microelectrode devices 1 except the first microelectrode device 1, the input terminal is coupled to the output terminal of the previous microelectrode device 1.

In this embodiment, each of the microelectrode devices 1 has the structure and the functions as those described in the first embodiment. Please note that the microelectrode devices 1 of the microfluidic chip 2 connect in a series, so each of the microelectrode devices 1 except the first microelectrode device 1 receives the input signal DI through the microelectrode device(s) 1 arranged ahead, and each of the microelectrode devices 1 except the last microelectrode device 1 provides the output signal DO through the microelectrode device(s) 1 arranged behind.

Figure 2C:
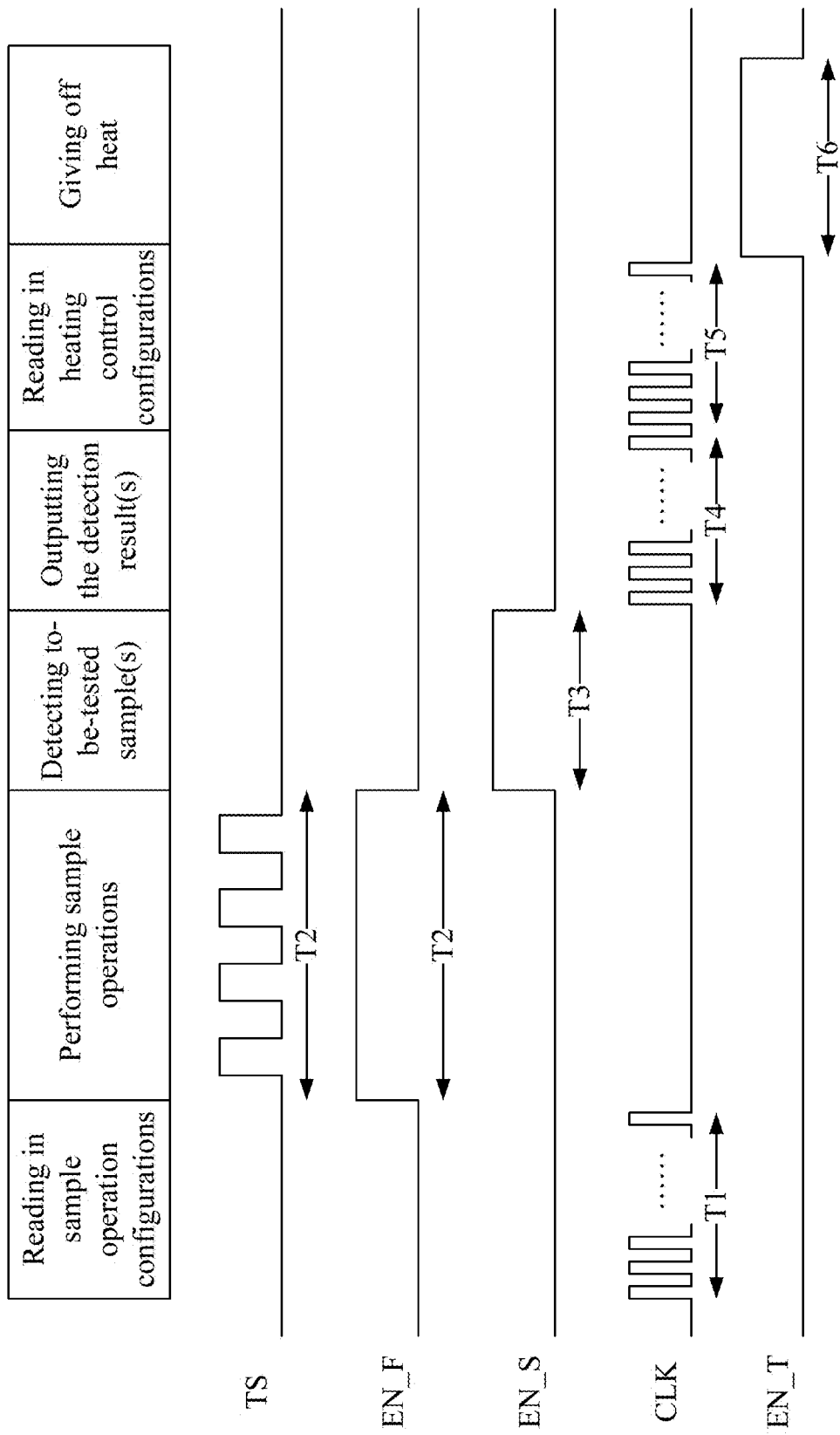
FIG. 2C illustrates the timing diagram of the signals that may be adopted to control the actions of the microfluidic chip 2 within an examination cycle in some embodiments.

In some embodiments, the timing diagram of the signals shown in FIG. 2C may be adopted to control the actions of the microelectrode devices 1 of the microfluidic chip 2 within an examination cycle. Similarly, an examination cycle may comprise the enabling time intervals T1, T2, T3, T4, T5, T6, wherein the enabling time interval T2 is later than the enabling time interval T1, the enabling time interval T3 is later than the enabling time interval T2, the enabling time interval T4 is later than the enabling time interval T3, the enabling time interval T5 is later than the enabling time interval T4, and the enabling time interval T6 is later than the enabling time interval T5. As shown in FIG. 2C, the clock CLK corresponds to the enabling time intervals T1, T4, T5, the voltage signal VS and the microfluidic control signal EN_F both corresponds to the enabling time interval T2, the location control signal EN_S corresponds to the enabling time interval T3, and the heating control signal EN_T corresponds to the enabling time interval T6. Please note that the voltage level of a signal (e.g., the clock CLK, the voltage signal VS, the microfluidic control signal EN_F, the location control signal EN_S, and the heating control signal EN_T) may be high in the corresponding enabling time interval, and the voltage level of a signal in the corresponding non-enabling time interval must be low.

The actions performed by the microelectrode devices 1 of the microfluidic chip 2 under the control of this timing diagram of signals will be detailed in the following paragraphs.

In this embodiment, the storage circuits 155 of the microelectrode devices 1 individually reads in a sample operation configuration during the enabling time interval T1 of the clock CLK. To be more specific, the enabling time interval T1 has a plurality of sub-enabling time intervals, and the sub-enabling time intervals correspond to the storage circuits 155 of the microelectrode devices 1 one-to-one. That is, if the microfluidic chip 2 comprises N microelectrode devices 1, the enabling time interval T1 has N sub-enabling time intervals. N is a positive integer. Please note that the voltage level of the clock CLK may be high in the sub-enabling time intervals, and the voltage level of the clock CLK in the non-enabling time intervals must be low. Each of the storage circuits 155 reads in the corresponding sample operation configuration during the corresponding sub-enabling time interval. Each of the sample operation configurations is used for indicating the sample operation to be performed by the corresponding microfluidic control and location sensing circuit 151 during the enabling time interval T2.

Figure 2D:
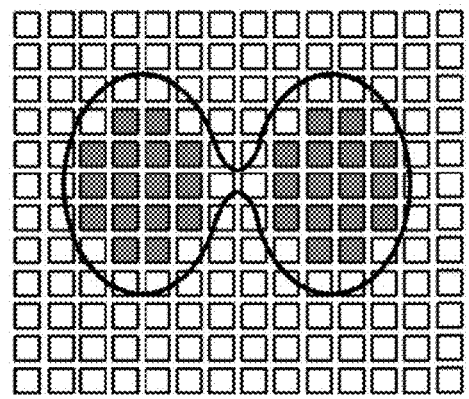
FIG. 2D is a schematic view of the sample operation configurations for cutting the to-be-tested sample.
Figure 2E:
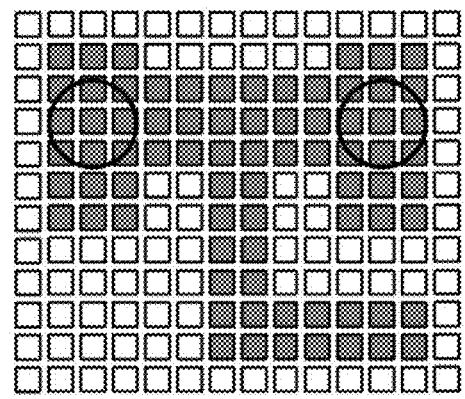
FIG. 2E is a schematic view of the sample operation configurations for moving and classifying the to-be-tested sample(s)
Figure 2F:
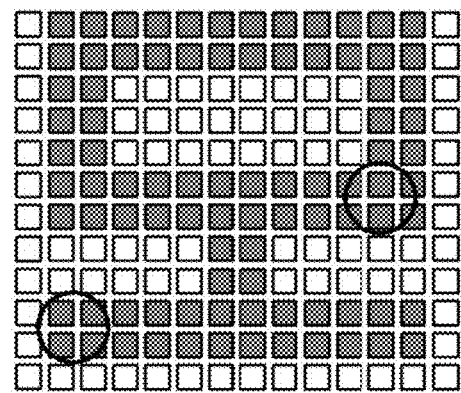
FIG. 2G, FIG. 2H, and FIG. 2I individually illustrates an example of the heating control configurations that can be read in by the storage circuits 155.
FIG. 2J illustrates another example of the heating control configurations that can be read in by the storage circuits 155.

For better comprehension, three examples regarding the sample operation configurations that can be read in by the N storage circuits 155 are shown in FIG. 2D, FIG. 2E, and FIG. 2F. Note that the content of FIG. 2D, FIG. 2E, and FIG. 2F are not intended to limit the scope of the present invention. In each of FIG. 2D, FIG. 2E, and FIG. 2F, the N squares represent the N sample operation configurations read in by the N storage circuits 155, wherein a grey square is used to instruct the corresponding microfluidic control and location sensing circuit 151 to act during the enabling time interval T2, and the white square is used to instruct the corresponding microfluidic control and location sensing circuit 151 not to act during the enabling time interval T2. The sample operation configurations shown in FIG. 2D, FIG. 2E, and FIG. 2F correspondingly enable the N microfluidic control and location sensing circuit 151 of the N microelectrode devices 1 to cut the to-be-tested sample, move and classify the to-be-tested sample(s), and move and mix the to-be-tested sample(s) during the enabling time interval T2.

Next, during the enabling time interval T2, the voltage level of the voltage signal VS provided to the top of the top plate 10 may be high. The microfluidic control and location sensing circuit 151 of each of the microelectrode devices 1 may perform a sample operation (i.e., a microfluidic operation) according to the corresponding sample operation configuration.

During the enabling time interval T3 of the location control signal EN_S, the microfluidic control and location sensing circuit 151 of each of the microelectrode devices 1 determines whether there is a to-be-tested sample. To be more specific, during the enabling time interval T3 of the location control signal EN_S, the microfluidic control and location sensing circuit 151 of each of the microelectrode devices 1 detects a capacitance value (not shown) between the top plate 10 and the corresponding microfluidic electrode 11 and stores the capacitance value in the corresponding storage circuit 155.

Following that, during the enabling time interval T4 of the clock CLK, the storage circuit 155 of each of the microelectrode devices 1 outputs the capacitance value stored therein (i.e., outputs the result of determining whether there is a to-be-tested sample). To be more specific, the enabling time interval T4 has a plurality of sub-enabling time intervals, and the sub-enabling time intervals correspond to the storage circuits 155 of the microelectrode devices 1 one-to-one. Please note that the voltage level of the clock CLK may be high in the sub-enabling time intervals, and the voltage level of the clock CLK in the non-enabling time intervals must be low. The storage circuit 155 of each of the microelectrode devices 1 outputs the corresponding capacitance value during the corresponding sub-enabling time interval.

Afterwards, during the enabling time interval T5 of the clock CLK, the storage circuit 155 of each of the microelectrode devices 1 reads in a corresponding heating control configuration (not shown) from the input signal DI. To be more specific, the enabling time interval T5 has a plurality of sub-enabling time intervals, and the sub-enabling time intervals correspond to the storage circuits 155 of the microelectrode devices 1 one-to-one. Please note that the voltage level of the clock CLK may be high in the sub-enabling time intervals, and the voltage level of the clock CLK in the non-enabling time intervals must be low. The storage circuit 155 of each of the microelectrode devices 1 reads in the corresponding heating control configuration during the corresponding sub-enabling time interval. Each of the heating control configurations is used for configuring a status of a switch of the corresponding temperature control circuit 153.

Figure 2G:
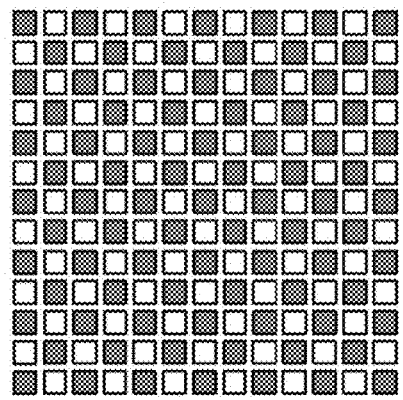
Figure 2H:
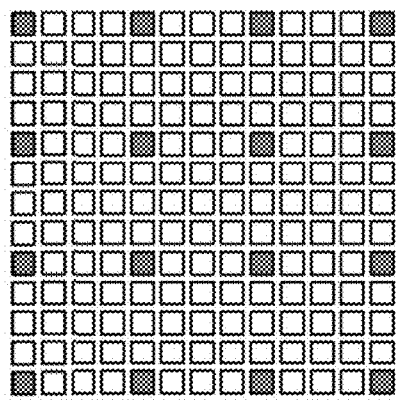
Figure 2I:
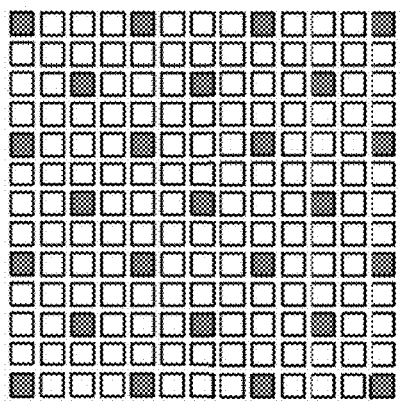

For better comprehension, three examples regarding the heating control configurations that can be read in by the N storage circuits 155 are shown in FIG. 2G, FIG. 2H, and FIG. 2I. It is noted that the content of FIG. 2G, FIG. 2H, and FIG. 2I do not intend to limit the scope of the present invention. In each of FIG. 2G, FIG. 2H, and FIG. 2I, the N squares represent the N heating control configurations read in by the N storage circuits 155, wherein a grey square is used to indicate that the status of the switch of the corresponding temperature control circuit 153 should be on during the enabling time interval T6 of the heating control signal EN_T, and a white square is used to indicate that the status of the switch of the corresponding temperature control circuit 153 should be off during the enabling time interval T6 of the heating control signal EN_T. A comparison of the three examples shown in FIG. 2G, FIG. 2H, and FIG. 2I follows. Since the heating control configurations shown in FIG. 2G will make more temperature control circuits 153 have their switch on, a higher temperature will be reached after heating up based on the heating control configurations. In addition, since the heating control configurations shown in FIG. 2G will make more temperature control circuits 153 have their switch off, a lower temperature will be reached after heating up based on the heating control configurations.

Next, during the enabling time interval T6 of the heating control signal EN_T, the temperature control circuit 153 of each of the microelectrode devices 1 configures the status of the switch of the corresponding temperature control circuit 153 according to the heating control configuration. If the heating control configuration indicates that the status of the switch of the corresponding temperature control circuit 153 should be on (e.g., the numerical value of the heating control configuration is "1"), the corresponding temperature control circuit 153 configures its switch to be on so that the corresponding heating electrode 13 can give off heat. If the heating control configuration indicates that the status of the switch of the corresponding temperature control circuit 153 should be off (e.g., the numerical value of the heating control configuration is "0"), the corresponding temperature control circuit 153 configures its switch to be off so that the corresponding heating electrode 13 does not function (i.e., give off no heat). By the previously mentioned mechanisms, the microfluidic chip 2 can reach a particular temperature to perform a particular microfluidic examination.

Figure 2J:
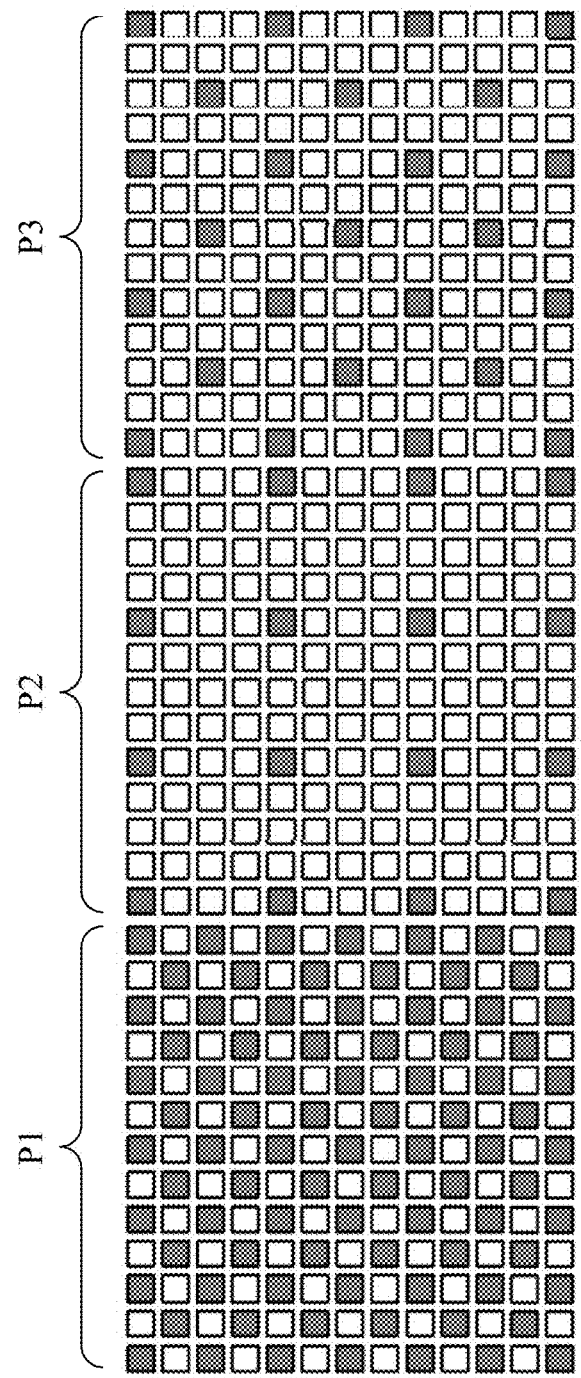

In some embodiments, the microfluidic chip 2 may be used in more complicated microfluidic examinations. For those embodiments, during the enabling time interval T5, the storage circuits 155 of the microelectrode devices 1 may read in the heating control configurations shown in FIG. 2J of the like. Specifically, in those embodiments, the microelectrode devices 1 is divided into a plurality of groups (e.g., in the example shown in FIG. 2J, there are three groups), and the heating control configurations read in by the storage circuits 155 of distinct groups are different. For each of the groups, the heating control configurations read in by the corresponding storage circuits 155 correspond to a heating pattern, and the heating patterns P1, P2, P3 of the groups are different as shown in FIG. 2J. Since distinct groups correspond to different heating patterns, different temperatures may be reached on the single microfluidic chip 2 so as to perform different microfluidic examinations.

According to the above descriptions, the microelectrode dot array 21 of the microfluidic chip 2 comprises a plurality of microelectrode devices 1 connected in series, and the microfluidic control and location sensing circuit 151, the temperature control circuit 153, and the storage circuit 155 comprised in each of the microelectrode devices 1 may receive different signals. With the aforementioned characteristics, each of the signals may be designated a corresponding enabling time interval, different sample operation configurations and different heating control configurations may be provided to different microelectrode devices 1 to enable the microfluidic chip 2 to perform more complicated microfluidic examinations. Hence, when performing microfluidic examinations by the microfluidic chip 2, examination temperature can be adjusted flexibly for different examination procedures; that is, the microfluidic chip 2 can be applied to various fields and various examination procedures.

Figure 3:
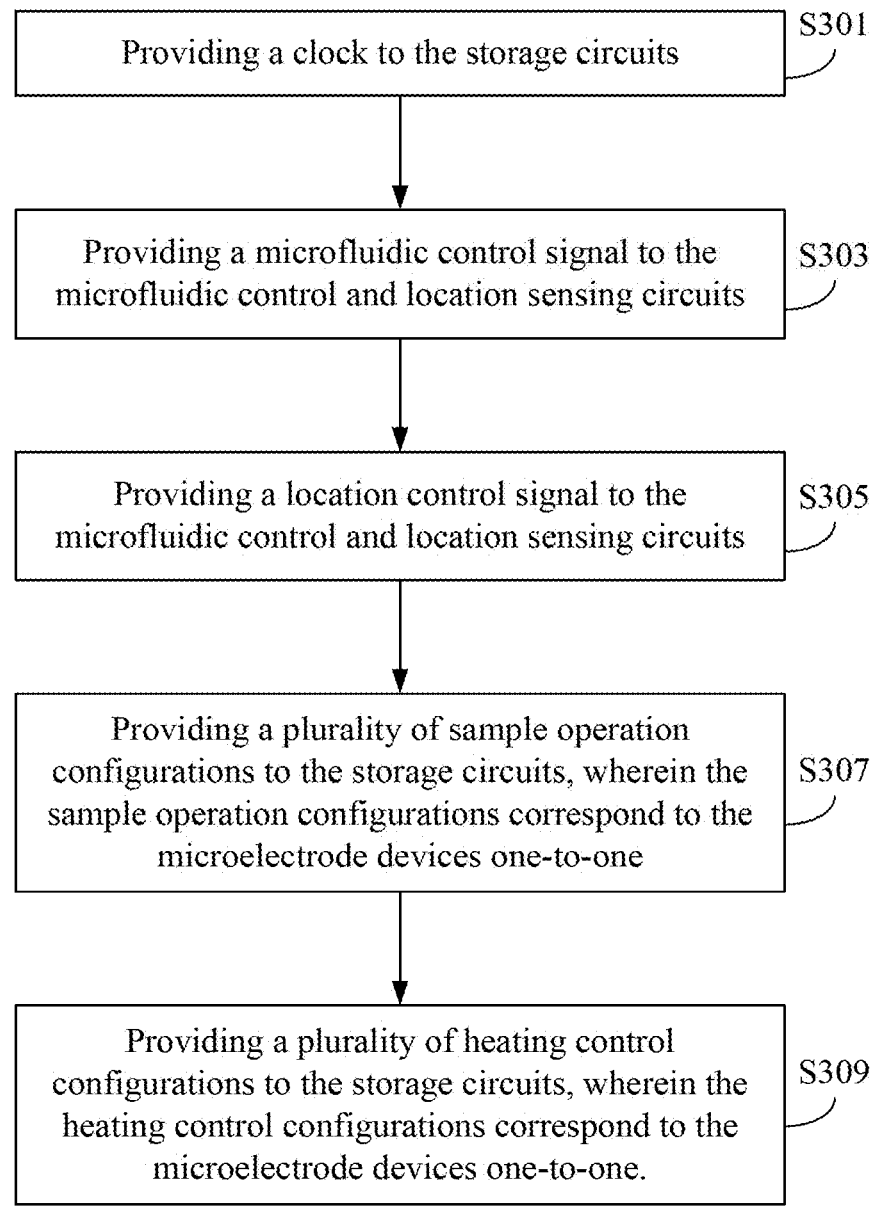
FIG. 3 illustrates the main flowchart of the microfluidic examination method in the third embodiment of the present invention.

The third embodiment of the present invention is a microfluidic examination method, which is for use in the microfluidic chip 2 as described in the second embodiment. The main flowchart of the microfluidic examination method is illustrated in FIG. 3, which comprises steps S301, S303, S305, S307, and S309 at a minimum.

Step S301 is executed for providing a clock to the storage circuits 155 of the microelectrode devices 1 of the microfluidic chip 2 (e.g., provided by an electronic computing apparatus). Step S303 is executed for providing a microfluidic control signal to the microfluidic control and location sensing circuits 151 of the microelectrode devices 1 of the microfluidic chip 2 (e.g., provided by an electronic computing apparatus). Step S305 is executed for providing a location control signal to the microfluidic control and location sensing circuits 151 of the microelectrode devices 1 of the microfluidic chip 2 (e.g., provided by an electronic computing apparatus). Step S307 is executed for providing a plurality of sample operation configurations to the storage circuits 155 of the microelectrode devices 1 of the microfluidic chip 2 (e.g., provided by an electronic computing apparatus), wherein the sample operation configurations correspond to the microelectrode devices 1 one-to-one. Step S309 is executed for providing a plurality of heating control configurations to the storage circuits 155 of the microelectrode devices 1 of the microfluidic chip 2 (e.g., provided by an electronic computing apparatus), wherein the heating control configurations correspond to the microelectrode devices 1 one-to-one.

Please note that the order for executing the previously mentioned steps S301, S303, S305, S307, and S309 is not restricted by the present invention. Each of the storage circuits reads in the corresponding sample operation configuration during a first enabling time interval of a clock. Each of the microfluidic control and location sensing circuits performs a corresponding sample operation according to the corresponding sample operation configuration during a second enabling time interval of the microfluidic control signal, wherein the second enabling time interval is later than the first enabling time interval. Each of the microfluidic control and location sensing circuits detects a corresponding capacitance value between the top plate and the corresponding microfluidic electrode and stores the corresponding capacitance value in the corresponding storage circuit during a third enabling time interval of the location control signal, wherein the third enabling time interval is later than the second enabling time interval. Each of the storage circuits outputs the corresponding capacitance value during a fourth enabling time interval of the clock, wherein the fourth enabling time interval is later than the third enabling time interval. Each of the storage circuits reads in a corresponding heating control configuration during a fifth enabling time interval of the clock, wherein the fifth enabling time interval is later than the fourth enabling time interval. Each of the temperature control circuits determines a status of a switch of the corresponding temperature control circuit according to the corresponding heating control configuration during a sixth enabling time interval of a heating control signal, wherein the sixth enabling time interval is later than the fifth enabling time interval.

In addition to the previously mentioned steps, the microfluidic examination method of the third embodiment can execute other steps to enable the microfluidic chip 2 to have the same functions and deliver the same technical effects as those described in the second embodiment. How the microfluidic examination method of the third embodiment executes those operations and steps, has the same functions, and delivers the same technical effects will be readily appreciated by a person having ordinary skill in the art based on the above explanation of the second embodiment, and thus will not be further described herein.

According to the microelectrode device provided by the present invention, the control circuit therein comprises a microfluidic control and location sensing circuit, a temperature control circuit, and a storage circuit, and the microfluidic control and location sensing circuit, the temperature control circuit, and the storage circuit may receive different signals. Therefore, each of the signals may be designated a corresponding enabling time interval to perform operations related to the microfluidic examination (including reading in sample operation configuration, performing a sample operation, detecting a to-be-tested sample, outputting the detection result regarding the to-be-tested sample, reading in the heating control configuration, and giving off heat to the to-be-tested sample). The microfluidic chip provided by the present invention comprises a microelectrode dot array having a plurality of microelectrode devices connected in a series. Since the microfluidic control and location sensing circuit, the temperature control circuit, and the storage circuit comprised in each of the microelectrode devices may receive different signals, each of the signals may be designated a corresponding enabling time interval and different sample operation configurations and different heating control configurations may be provided to different microelectrode devices to enable the microfluidic chip to perform more complicated microfluidic examinations. Therefore, when performing microfluidic examinations by the microelectrode devices, microfluidic chips, and microfluidic examination methods of the present invention, examination temperature can be adjusted flexibly for different examination procedures. As a result, the microelectrode devices, microfluidic chips, and microfluidic examination methods provided by the present invention can be applied to various fields and various examination procedures.

The above disclosure is related to the detailed technical contents and inventive features thereof. A person having ordinary skill in the art may proceed with a variety of modifications and replacements based on the disclosures and suggestions of the invention as described without departing from the characteristics thereof. Nevertheless, although such modifications and replacements are not fully disclosed in the above descriptions, they have been substantially covered in the following claims as appended.

What is claimed is:

1. A microelectrode device, comprising:
   a microfluidic electrode, being configured for being arranged under a top plate;
   a heating electrode, being arranged under the microfluidic electrode; and
   a control circuit, being arranged under the heating electrode and comprising:
   a temperature control circuit, being coupled to the heating electrode;
   a storage circuit being configured for reading in a sample operation configuration during a first enabling time interval of a clock; and
   a microfluidic control and location sensing circuit, being coupled to the microfluidic electrode, being configured for performing a sample operation according to the sample operation configuration during a second enabling time interval of a microfluidic control signal, and being configured for detecting a capacitance value between the top plate and the microfluidic electrode and store the capacitance value in the storage circuit during a third enabling time interval of a location control signal,
   wherein the storage circuit is further configured to output the capacitance value during a fourth enabling time interval of the clock and read in a heating control configuration during a fifth enabling time interval of the clock,
   wherein the temperature control circuit is further configured to determine a status of a switch of the temperature control circuit according to the heating control configuration during a sixth enabling time interval of a heating control signal.

2. The microelectrode device of claim 1, wherein the heating electrode is configured to give off heat when the status of the switch of the temperature control circuit is on.

3. The microelectrode device of claim 1, wherein the heating electrode is configured to give off no heat when the status of the switch of the temperature control circuit is off.

4. The microelectrode device of claim 1, wherein the second enabling time interval is later than the first enabling time interval, the third enabling time interval is later than the second enabling time interval, the fourth enabling time interval is later than the third enabling time interval, the fifth enabling time interval is later than the fourth enabling time interval, and the sixth enabling time interval is later than the fifth enabling time interval.

5. A microfluidic chip, comprising:
a top plate; and
a microelectrode dot array, being arranged under the top plate and comprising a plurality of microelectrode devices connected in a series,
wherein each of the microelectrode devices comprises:
a microfluidic electrode, being arranged under the top plate;
a heating electrode, being arranged under the microfluidic electrode; and
a control circuit, being arranged under the heating electrode and comprising:
  a temperature control circuit, being coupled to the heating electrode;
  a storage circuit, being configured for reading in a sample operation configuration during a first enabling time interval of a clock; and
  a microfluidic control and location sensing circuit, being coupled to the microfluidic electrode, being configured for performing a sample operation according to the sample operation configuration during a second enabling time interval of a microfluidic control signal, and being configured for detecting a capacitance value between the top plate and the microfluidic electrode and store the capacitance value in the storage circuit during a third enabling time interval of a location control signal,
wherein the storage circuit is further configured to output the capacitance value during a fourth enabling time interval of the clock and reads in a heating control configuration during a fifth enabling time interval of the clock,
wherein the temperature control circuit is further configured to determine a status of a switch of the temperature control circuit according to the heating control configuration during a sixth enabling time interval of a heating control signal.

6. The microfluidic chip of claim 5, wherein each of the microelectrode devices has an input terminal and an output terminal,
wherein for each of the microelectrode devices except the first microelectrode device, the input terminal is coupled to the output terminal of the previous microelectrode device.

7. The microfluidic chip of claim 5, wherein the first enabling time interval has a plurality of sub-enabling time intervals, the sub-enabling time intervals correspond to the storage circuits of the microelectrode devices one-to-one, and each of the storage circuit is configured to read in the corresponding sample operation configuration during the corresponding sub-enabling time interval.

8. The microfluidic chip of claim 5, wherein the fourth enabling time interval has a plurality of sub-enabling time intervals, the sub-enabling time intervals correspond to the storage circuits of the microelectrode devices one-to-one, and each of the storage circuit is configured to output the corresponding capacitance value during the corresponding sub-enabling time interval.

9. The microfluidic chip of claim 5, wherein the fifth enabling time interval has a plurality of sub-enabling time intervals, the sub-enabling time intervals correspond to the storage circuits of the microelectrode devices one-to-one, and each of the storage circuit is configured to read in the corresponding heating control configuration during the corresponding sub-enabling time interval.

10. The microfluidic chip of claim 5, wherein for each of the microelectrode devices, the corresponding heating electrode is configured to give off heat when the status of the switch of the corresponding temperature control circuit is on.

11. The microfluidic chip of claim 5, wherein for each of the microelectrode devices, the corresponding heating electrode is configured to give off no heat when the status of the switch of the corresponding temperature control circuit is off.

12. The microfluidic chip of claim 5, wherein the second enabling time interval is later than the first enabling time interval, the third enabling time interval is later than the second enabling time interval, the fourth enabling time interval is later than the third enabling time interval, the fifth enabling time interval is later than the fourth enabling time interval, and the sixth enabling time interval is later than the fifth enabling time interval.

13. The microfluidic chip of claim 5, wherein the microelectrode devices are divided into a plurality of groups,
wherein for each of the groups, the heating control configurations read in by the corresponding storage circuits correspond to a heating pattern,
wherein the heating patterns of the groups are different.

14. A microfluidic examination method for use in a microfluidic chip, the microfluidic chip comprising a top plate and a microelectrode dot array, the microelectrode dot array being arranged under the top plate, the microelectrode dot array comprising a plurality of microelectrode devices connected in a series, each of the microelectrode devices comprising a microfluidic electrode, a heating electrode, and a control circuit, each of the microfluidic electrodes being arranged under the top plate, each of the heating electrodes being arranged under the corresponding microfluidic electrode, each of the control circuits being arranged under the corresponding heating electrode, each of the control circuits comprising a microfluidic control and location sensing circuit, a storage circuit, and a temperature control circuit, each of the microfluidic control and location sensing circuits being coupled to the corresponding microfluidic electrode, each of the temperature control circuits being coupled to the corresponding heating electrode, and the microfluidic examination method comprising the following steps:
  (a) providing a clock to the storage circuits;
  (b) providing a microfluidic control signal to the microfluidic control and location sensing circuits;
  (c) providing a location control signal to the microfluidic control and location sensing circuits;
  (d) providing a plurality of sample operation configurations, wherein the sample operation configurations correspond to the microelectrode devices one-to-one; and
  (e) providing a plurality of heating control configurations, wherein the heating control configurations correspond to the microelectrode devices one-to-one,
wherein each of the storage circuits reads in the corresponding sample operation configuration during a first enabling time interval of a clock,
wherein each of the microfluidic control and location sensing circuits performs a corresponding sample operation according to the corresponding sample operation configuration during a second enabling time interval of the microfluidic control signal,
wherein each of the microfluidic control and location sensing circuits detects a corresponding capacitance value between the top plate and the corresponding microfluidic electrode and stores the corresponding capacitance value in the corresponding storage circuit during a third enabling time interval of the location control signal, wherein each of the storage circuits outputs the corresponding capacitance value during a fourth enabling time interval of the clock, each of the storage circuits reads in a corresponding heating control configuration during a fifth enabling time interval of the clock, and each of the temperature control circuits determines a status of a switch of the corresponding temperature control circuit according to the corresponding heating control configuration during a sixth enabling time interval of a heating control signal.

15. The microfluidic examination method of claim 14, wherein the first enabling time interval has a plurality of sub-enabling time intervals, and the sub-enabling time intervals correspond to the storage circuit of the microelectrode devices one-to-one so that each of the storage circuit reads in the corresponding sample operation configuration during the corresponding sub-enabling time interval.

16. The microfluidic examination method of claim 14, wherein the fourth enabling time interval has a plurality of sub-enabling time intervals, and the sub-enabling time intervals correspond to the storage circuit of the microelectrode devices one-to-one so that each of the storage circuit outputs the corresponding capacitance value during the corresponding sub-enabling time interval.

17. The microfluidic examination method of claim 14, wherein the fifth enabling time interval has a plurality of sub-enabling time intervals, and the sub-enabling time intervals correspond to the storage circuit of the microelectrode devices one-to-one so that each of the storage circuit reads in the corresponding heating control configuration during the corresponding sub-enabling time interval.

18. The microfluidic examination method of claim 14, wherein the second enabling time interval is later than the first enabling time interval, the third enabling time interval is later than the second enabling time interval, the fourth enabling time interval is later than the third enabling time interval, the fifth enabling time interval is later than the fourth enabling time interval, and the sixth enabling time interval is later than the fifth enabling time interval.

19. The microfluidic examination method of claim 14, wherein the microelectrode devices is divided into a plurality of groups,
wherein for each of the groups, the heating control configurations read in by the corresponding storage circuits correspond to a heating pattern,
wherein the heating patterns of the groups are different.

* * * * *